(12) United States Patent
Bukshpan et al.

(10) Patent No.: US 10,325,379 B2
(45) Date of Patent: Jun. 18, 2019

(54) SWEAT PORES IMAGING METHOD AND DEVICE

(71) Applicants: Shmuel Bukshpan, Ramat Hasharon (IL); Uriel Halavee, Tel Aviv (IL); Arie Heiman, Sde Warburg (IL)

(72) Inventors: Shmuel Bukshpan, Ramat Hasharon (IL); Uriel Halavee, Tel Aviv (IL); Arie Heiman, Sde Warburg (IL)

(*) Notice: Subject to any disclaimer, the term of this patent is extended or adjusted under 35 U.S.C. 154(b) by 0 days.

(21) Appl. No.: 15/264,653

(22) Filed: Sep. 14, 2016

(65) Prior Publication Data

US 2017/0116492 A1    Apr. 27, 2017

Related U.S. Application Data

(63) Continuation-in-part of application No. 15/212,236, filed on Jul. 17, 2016.

(60) Provisional application No. 62/232,446, filed on Sep. 25, 2015, provisional application No. 62/231,855, filed on Jul. 20, 2015.

(51) Int. Cl.
*G06K 9/00* (2006.01)
*G06T 7/70* (2017.01)
*A61B 5/1171* (2016.01)
*A61B 5/00* (2006.01)

(52) U.S. Cl.
CPC .............. *G06T 7/70* (2017.01); *A61B 5/1171* (2016.02); *A61B 5/4887* (2013.01); *G06K 9/00885* (2013.01); *A61B 5/0077* (2013.01); *A61B 5/4266* (2013.01); *A61B 2562/029* (2013.01)

(58) Field of Classification Search
CPC .......... G06K 9/00885–9/00926; A61B 5/1171; A61B 5/4887; A61B 5/4266; A61B 5/0077; A61B 2562/029
See application file for complete search history.

(56) References Cited

U.S. PATENT DOCUMENTS

| | | | | |
|---|---|---|---|---|
| 2003/0044051 A1* | 3/2003 | Fujieda | .............. | G06K 9/00067 382/124 |
| 2013/0100267 A1* | 4/2013 | Baek | .................. | G06K 9/00067 348/77 |
| 2014/0037158 A1* | 2/2014 | McNulty | ............ | G06K 9/00013 382/125 |
| 2014/0196131 A1* | 7/2014 | Lee | ......................... | G06F 21/35 726/7 |
| 2015/0278577 A1* | 10/2015 | Cho | ........................ | G06F 3/041 382/124 |
| 2015/0329656 A1* | 11/2015 | Kim | ...................... | C08F 138/00 524/547 |

(Continued)

*Primary Examiner* — Aaron W Carter
(74) *Attorney, Agent, or Firm* — Reches Patents

(57) ABSTRACT

A biometric device that may include a sensor that reacts to a chemical element associated with a sweat gland; wherein when the sensor is contacted by an area of a skin of a person, an image that comprises information about locations of sweat glands within the area of the skin of the person is generated by the sensor; an image processor that is configured to generate an authentication result by comparing between (a) the information of the image generated by the sensor and (b) reference information of locations of sweat glands of a given person; wherein the authentication result indicates whether the person is the given person; and a communication module for communicating an authentication result indication.

33 Claims, 14 Drawing Sheets

Acquiring, by an image sensor and when a moisture sensor is contacted by an area of a skin of a person, an image that includes visual information about locations of sweat glands within the area of the skin of the person. The moisture sensor may include a hydrochromatic compound processing the image to provide a result. 110

Processing the image to provide a result. The processing may include at least one of the following: (a) generating a sweat glands map, (b) authenticating a person based on the image, (c) authenticating a person based on the sweat glands map, (d) authenticating a person based on the locations of the sweat glands and based on additional visual information included in the image. 120

(56) References Cited

U.S. PATENT DOCUMENTS

| | | | |
|---|---|---|---|
| 2015/0347805 A1* | 12/2015 | McNulty | G06K 9/00033 |
| | | | 382/124 |
| 2016/0034679 A1* | 2/2016 | Yun | G06F 1/163 |
| | | | 340/5.83 |
| 2016/0071101 A1* | 3/2016 | Winarski | G06Q 20/3829 |
| | | | 705/71 |
| 2016/0171280 A1* | 6/2016 | Han | G06K 9/00067 |
| | | | 348/77 |
| 2017/0032202 A1* | 2/2017 | Halavee | A61B 5/4887 |
| 2017/0116492 A1* | 4/2017 | Bukshpan | A61B 5/1171 |
| 2017/0190814 A1* | 7/2017 | Kim | C08F 138/02 |

* cited by examiner

Acquiring, by an image sensor and when a moisture sensor is contacted by an area of a skin of a person, an image that includes visual information about locations of sweat glands within the area of the skin of the person. The moisture sensor may include a hydrochromatic compound processing the image to provide a result. 110

Processing the image to provide a result. The processing may include at least one of the following: (a) generating a sweat glands map, (b) authenticating a person based on the image, (c) authenticating a person based on the sweat glands map, (d) authenticating a person based on the locations of the sweat glands and based on additional visual information included in the image. 120

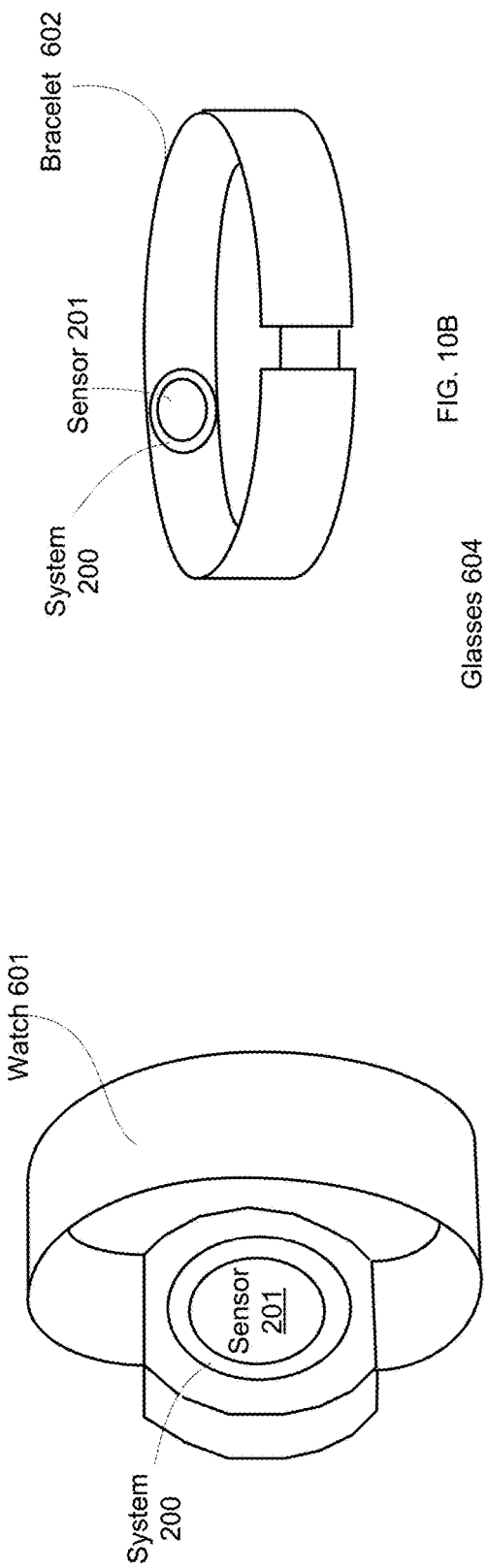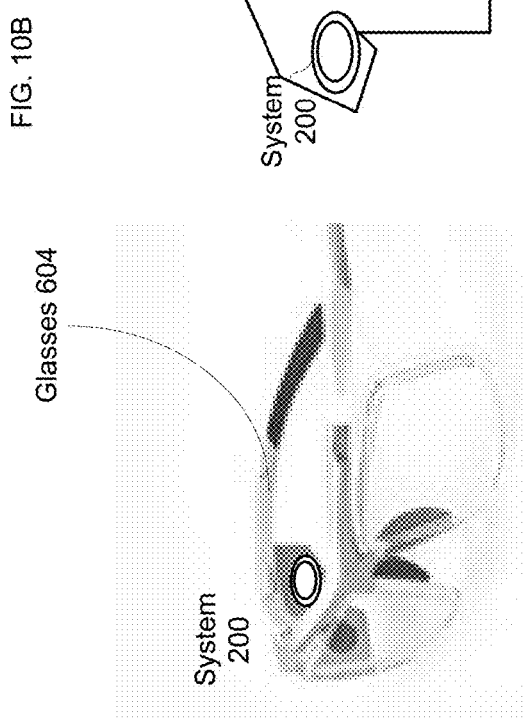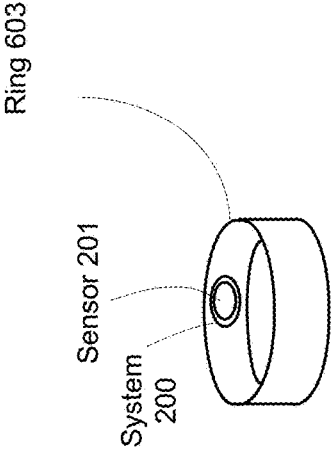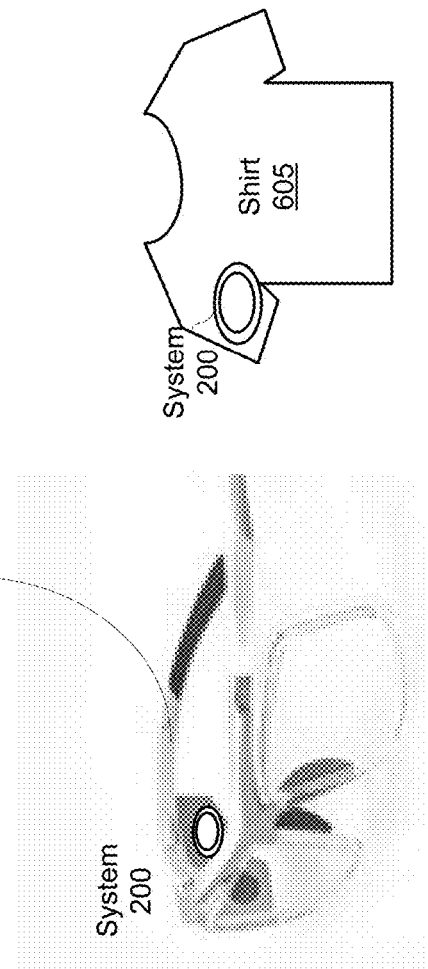

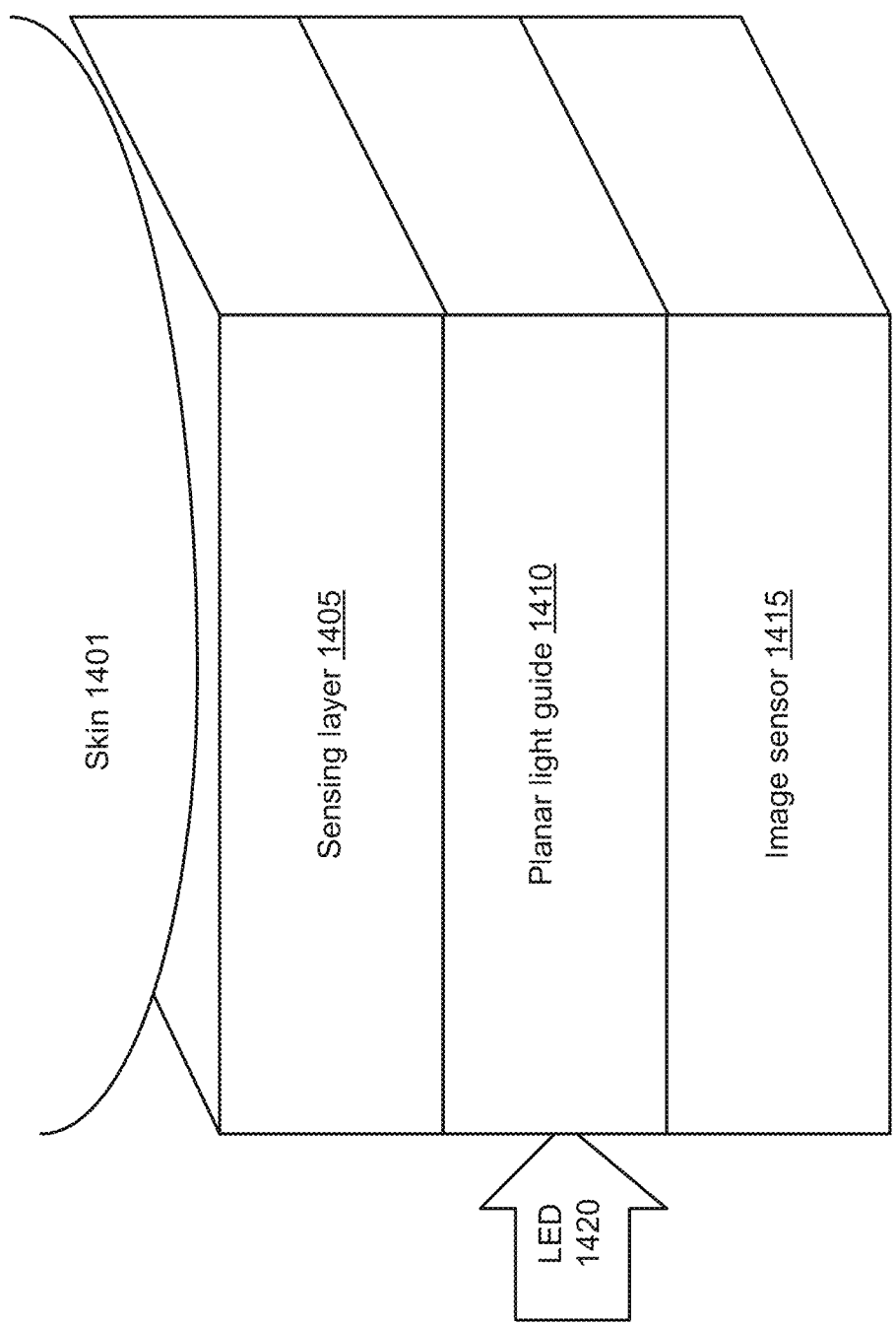

SWEAT PORES IMAGING METHOD AND DEVICE

CROSS REFERENCE TO RELATED APPLICATIONS

This application claims priority from U.S. provisional patent Ser. No. 62/232,446 filing date Sep. 25, 2015 which is incorporated herein by reference.

This application is a continuation in part of U.S. patent application Ser. No. 15/212,236 filing date Jul. 17, 2015 which claims priority from US provisional patent filing date Jul. 17, 2015, Ser. No. 62/231,855 which are incorporated herein by reference.

BACKGROUND OF THE INVENTION

To keep confidentially of digital material people use password to block unauthorized person to access to that material, typical secure material can be: access to computer, unlock mobile phones, open confidential files, online banking, online payment, mobile payment, open the entrance door to home or office, etc.

In order to access to that secure material, the user needs to type the correct password. In some cases, there is a special card like a credit card that the user needs to slide it or to locate it near to the card reader. The card reader identifies if the card holder has permission to access to the confidential material or not. In some other cases people use fingerprint to enable access. In this case the user need to put his relevant finger on a fingerprint reader which analyzes and identifies if the fingerprint of the user is valid and has permission to access. All this kind of access procedures are very inconvenient. For example; In case of typing password, most of the people use different passwords for different accounts which means that the user needs to remember different password for different access points, which can be very annoying. In case of credit card most of people hold it in their wallet and in order to use it, they need to find the relevant card and slide it on the access reader.

SUMMARY

According to an embodiment of the invention there may be provided a biometric device that may include a sensor that may react to a chemical element associated with a sweat gland; and when the sensor may be contacted by an area of a skin of a person, an image that may include visual information about locations of sweat glands within the area of the skin of the person.

The sensor may be a sensor that may react with a chemical element included in sweat.

The sensor may be a moisture sensor that may include a hydrochromic compound.

The image may include additional visual information about the area of the skin.

The additional visual information may include topographic information related to the area of the skin.

The additional visual information may include information about skin patterns.

The biometric device may include an authentication unit that may be configured to authenticate a person based on the visual information about the locations of the sweat glands and based on the additional visual information.

The moisture sensor may include a transparent polymer layer that may be doped with the hydrochromic compound.

The moisture sensor may incorporate a planar transparent light guide for illumination with an external light source. The hydrochromic polymer layer may be deposited on a photoactive surface of the image sensor.

The hydrochromic polymer layer may be deposited on an optical component of the image sensor.

The hydrochromic layer may be deposited on a transparent polymer substrate and attached to the photoactive surface of the image sensor.

The biometric device where the hydrochromic layer may be deposited on a transparent polymer substrate doped with a light emitting phosphor and may be attached to a photoactive surface of the image sensor.

The skin biometric device where the hydrochromic layer may be deposited on an imaging light guide attached to the image sensor.

The moisture sensor may be transparent.

The biometric device may include an image processor that may be configured to process the image to generate a sweat glands map.

The biometric device may include an authentication unit that may be configured to process the image to authenticate a person.

The hydrochromic layer may be coated by a thin porous antifouling layer.

The biometric device may include a wireless communication module.

The field of view of the sensor may or may not exceed one square centimeter.

The field of view of the sensor exceeds one square centimeter.

According to an embodiment of the invention there may be provided a method for acquiring biometric information, the method may include acquiring, by an image sensor and when a sensor may be contacted by an area of a skin of a person, an image that may include visual information about locations of sweat glands within the area of the skin of the person; wherein the sensor may react to a chemical element associated with a sweat gland.

According to an embodiment of the invention there may be provided a biometric device that may include a sensor that reacts to a chemical element associated with a sweat gland; wherein when the sensor may be contacted by an area of a skin of a person, the sensor may be configured to acquire an image that may include information about locations of sweat glands within the area of the skin of the person; an image processor that may be configured to generate an authentication result by comparing between (a) the information of the image generated by the sensor and (b) reference information of locations of sweat glands of a given person; wherein the authentication result indicates whether the person may be the given person; and a communication module for communicating an authentication result indication.

The biometric device may include a memory module for storing encrypted reference information; and a decryption unit that may be configured to decrypt the encrypted reference information to provide the reference information.

The biometric device may include an encryption unit may be configured to encrypt the reference information to provide the encrypted reference information.

The image processor may be configured to generate the reference information by processing the image generated by the sensor during a registration process.

The sensor may be configured to acquire an additional image of the area of the skin of the person; wherein the additional image may include additional information about locations of sweat glands within the area of the skin of the person; and wherein the image processor may be configured to verify the reference information by comparing between the reference information and the additional information.

The reference information may include a binary image; wherein the image processor may be configured to threshold the image generated by the sensor to provide a binary image and to compare the binary image to the reference binary image.

The reference information may include a reference image; wherein the image processor may be configured to calculate a correlation between the reference image and the image acquired by the sensor.

The communication module may be a short range wireless communication module.

The biometric device may include a controller that may be configured to trigger multiple authentication operations for acquiring multiple images of the area of the skin of the person and for generating multiple authentication results.

The sensor may be a sensor that reacts with a chemical element included in sweat.

The sensor may be a moisture sensor that may include a hydrochromatic compound.

The image may include additional visual information about the area of the skin.

The additional visual information may include topographic information related to the area of the skin.

The additional visual information may include information about skin patterns.

The image processor may be configured to generate the authentication result in response to the additional visual information.

The sensor may include a light guide.

The sensor may include a light guide that may be transparent and positioned between a sensing layer of the sensor and an image sensor of the sensor.

The biometric device may include a memory module that may be configured to store the image while the biometric device may be worn by the person and to delete the image once the biometric device may be removed from the person.

According to an embodiment of the invention there may be provided a method for biometric based authentication, the method may include generating, by a sensor that reacts to a chemical element associated with a sweat gland and when the sensor may be contacted by an area of a skin of a person, an image that may include information about locations of sweat glands within the area of the skin of the person; generating, by an image processor, an authentication result by comparing between (a) the information of the image generated by the sensor and (b) reference information of locations of sweat glands of a given person; wherein the authentication result indicates whether the person may be the given person; and communicating, by a communication module, an authentication result indication.

The method may include storing in a memory module encrypted reference information; and decrypting, by a decryption unit, the encrypted reference information to provide the reference information.

The method may include encrypting, by an encryption unit, the reference information to provide the encrypted reference information.

The method may include generating the reference information by processing the image generated by the sensor during a registration process.

The method may include acquiring, by the sensor, an additional image of the area of the skin of the person; wherein the additional image may include additional information about locations of sweat glands within the area of the skin of the person; and verifying the reference information by comparing between the reference information and the additional information.

The reference information may include a binary image; wherein the method may include thresholding the image generated by the sensor to provide a binary image and comparing the binary image to the reference binary image.

The reference information may include a reference image; wherein the method may include calculating a correlation between the reference image and the image acquired by the sensor.

The communicating of the authentication result indication may include short range wireless communicating the authentication result indication.

The method may include triggering, by a controller, multiple authentication operations for acquiring multiple images of the area of the skin of the person and for generating multiple authentication results.

The generating of the image involves reacting with a chemical element included in sweat.

The generating of the image involves reacting to moisture; wherein the sensor may include a hydrochromatic compound.

The image may include additional visual information about the area of the skin.

The additional visual information may include topographic information related to the area of the skin.

The additional visual information may include information about skin patterns.

The generating of the authentication result may be also responsive to the additional visual information.

The method may include preventing from acquiring additional images during a continuous period in which the sensor may be worn by the person.

The method may include storing the image in a memory module and deleting the image once the sensor may be removed from the person.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 6 illustrates a method according to an embodiment of the invention.

FIGS. 10A, 10B, 10C, 10D and 10E illustrates examples of systems and their environments;

FIG. 14 illustrate a device according to an embodiment of the invention.

DETAILED DESCRIPTION OF THE PRESENT INVENTION

Figure 1:
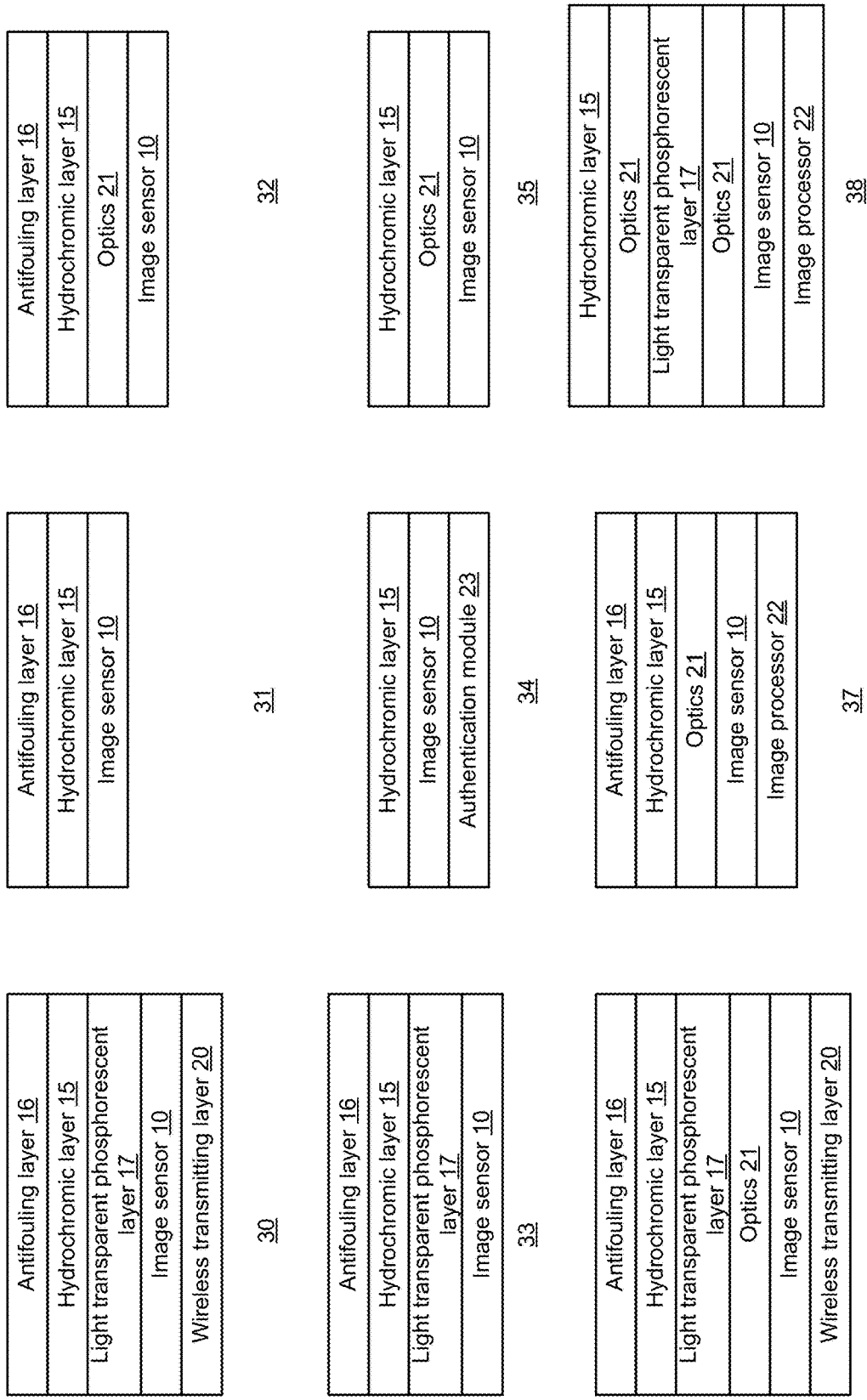
FIG. 1 illustrates biometric devices according to an embodiment of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

According to an embodiment of the invention there may be provided a device that may include and a method that may use a sensor that may react to a chemical element associated with a sweat gland. For simplicity of explanation the following text will refer to a sensor that is a humidity sensor. It should be noted that the sensor may use chemo chromic detection of chemicals in the sweat such as lactate and others, or any combination of humidity sensing and any other chemical element appearing in the sweat.

The terms "pores" and "glands" are used in an interchangeable manner.

Sweat glands are present on most of the human skin and distributed at varying concentration on different body regions. Their local density and exact location on the skin is unique and personal which makes a sweat gland map or print a powerful means of authentication.

There are provided methods and devices for acquisition of the sweat gland map on hydrochromic coating an image.

According to an embodiment of the invention there may be provided a low cost skin biometric device for imaging and mapping of sweat glands and registration of sweat glands distribution on skin for cosmetic, medical and authentication applications and specifically for combined imaging of sweat glands together with other skin identification marks for improved identification and verification.

The suggested device and methods provide a higher level of secure verification in comparison to prior art methods and devices—as the suggested method and devices provide an additional level of verification based on acquisition of a fingerprint based on moisture distribution which displays a map of sweat glands together with the standard fingerprint detection process. Such a map is much more difficult to forge than fingerprints.

In combination with fingerprint acquisition obtained by bringing the finger in contact with the surface of a moisture permeable polymer doped with a hydrochromic compound an image is generated which contains all three levels of authentication.

In an embodiment the current invention presents a device which comprises an image sensor such as a CCD or CMOS combined with a transparent polymer layer doped with a dispersion of reversible hydrochromic, colorimetric moisture indicating composition optimized for fast response both in acquisition and recovery (fast change in color and fast return to original state) for repeatable operation.

Many hydrochromic materials are known in the art and such materials can be used in this invention. They may consist of various salts as well as polymer dyes. Preferably, the hydrochromic material comprises cobalt chloride or copper chloride, cobalt chloride being the preferred. These hydrochromic materials can be incorporated in hydrophilic matrices like PVA, polyacrylamide, PEG etc. to produce hydrochromic sheets and layers.

The change of color on exposure to moisture can be irreversible for single use or reversible after evaporation.

The device when brought in contact with a skin area records the change in the moisture sensitive hydrochromic layer which corresponds to local moisture distribution and enables the simultaneous acquisition of the position of many sweat glands together with the local skin features, fingerprint ridge map, wrinkle map or local skin identification marks.

In one embodiment the hydrochromic polymer layer is deposited directly on the photosensitive surface of a CCD or CMOS image sensor by coating, adhesion, spraying, spin coating and other deposition methods known in the art.

In another embodiment the hydrochromic polymer layer is deposited on a transparent solid substrate mounted in direct contact with the image sensor photosensitive surface.

In another embodiment the solid substrate contains a light emitting phosphor or tiny waveguide or fiber optic which supplies illumination.

In some embodiments, the colorimetric hydrochromic layer of the device is overlaid by a thin transparent, porous, water permeable self-cleaning layer for prevention of fouling or any erasable layer.

In a further embodiment the device comprises a hydrochromic polymer layer deposited on a transparent substrate (glass, polymer or other) and mounted together with a photo camera, web camera, smart phone camera and enabled to acquire a sweat gland map image together with the skin features.

In a further embodiment the device is a standalone device enabled with wireless connectivity like Wi Fi, Bluetooth or NFC enabling the transfer of the image for image processing and analysis.

In a further embodiment the biometric device of invention is equipped with a light source and power source.

In a further embodiment the device is enabled with wireless charging.

The device of invention can be incorporated in any electronic device requiring authentication: computer, Smartphone, smart watch, teller machine, cash register, access control systems, lock etc.

In further embodiment the hydrochromic layer is deposited on an imaging light guide or fiber bundle coupled to the image sensor.

Figure 4:
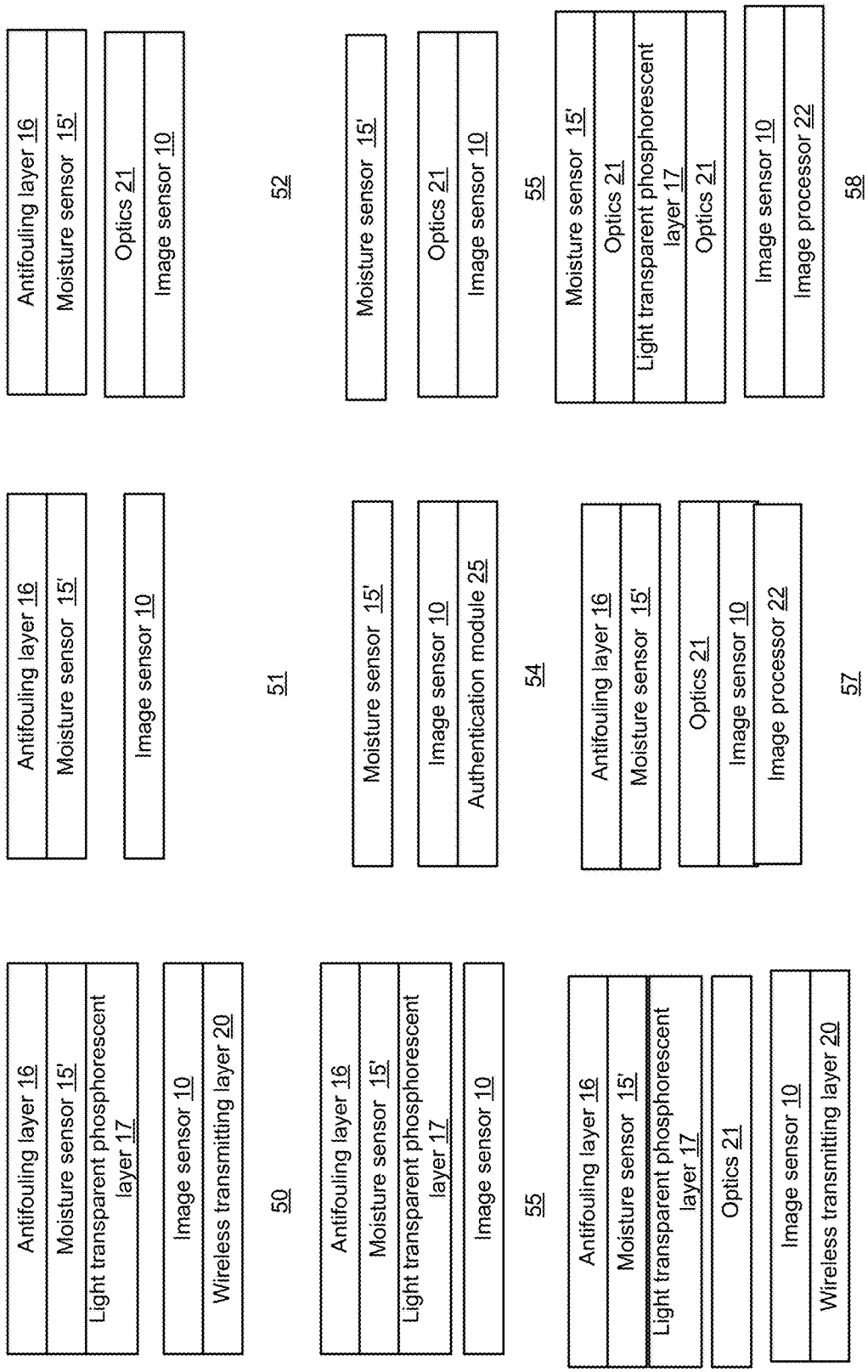
FIG. 4 illustrates biometric devices according to an embodiment of the invention.
Figure 5:
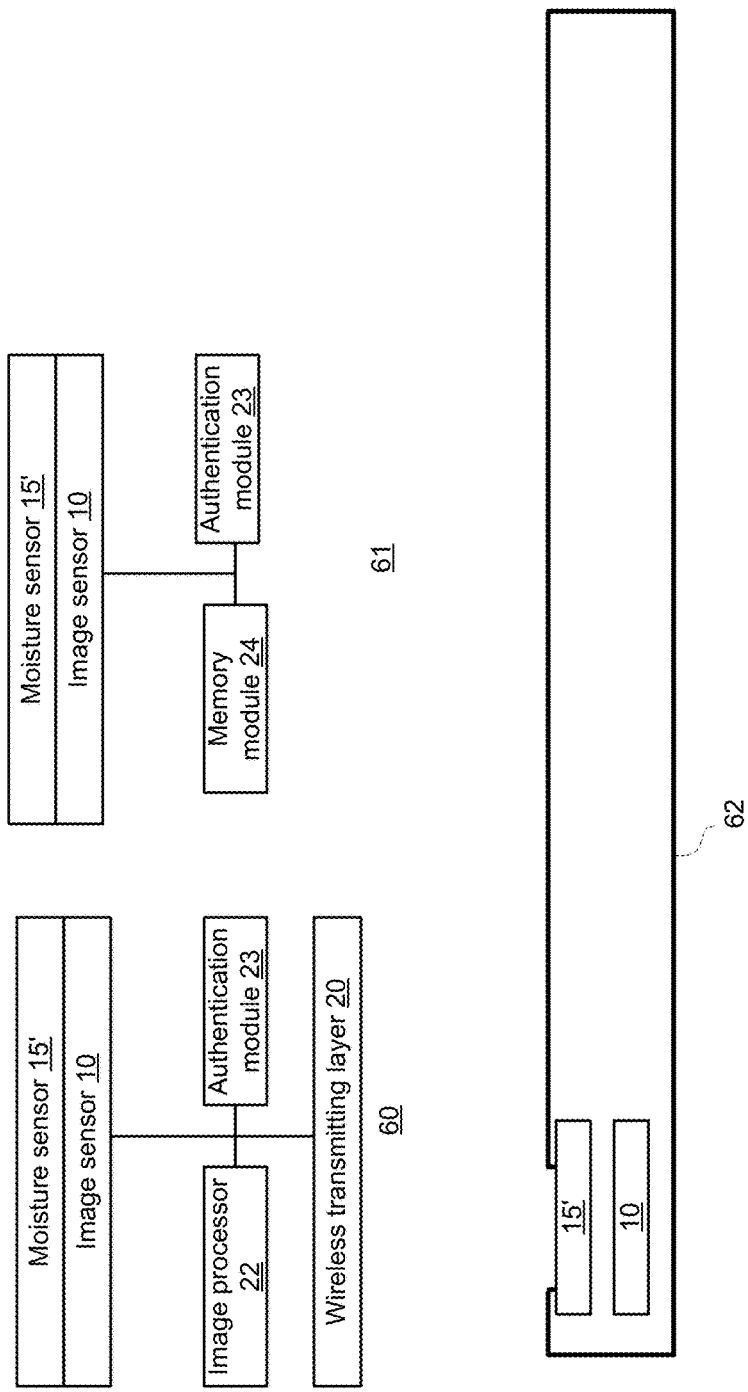
FIG. 5 illustrates biometric devices according to an embodiment of the invention.

FIGS. 1, 4 and 5 illustrate various biometric devices 30, 31, 32, 33, 34, 35, 36, 37, 38, 50, 51, 52, 53, 54, 55, 56, 57, 58, 60, 61 and 62 according to various embodiment of the invention.

Biometric device 30 includes the following sequence of elements: antifouling layer 16, hydrochromic layer 15, light transparent phosphorescent layer 17, image sensor 10 and wireless transmitting layer 20. The hydrochromic layer 15 is a non-limiting example of a moisture sensor that includes a hydrochromatic compound. The antifouling can be also done by erasable layer.

Biometric device 31 includes the following sequence of elements: antifouling layer 16, hydrochromic layer 15 and image sensor 10.

Biometric device 32 includes the following sequence of elements: antifouling layer 16, hydrochromic layer 15, optics 21 and image sensor 10. Optics 21 may be any optical lens or optical element for conveying, relaying, filtering, magnifying, manipulating radiation. The optics may include an optical guide, one or more lenses, spatial and/or spectral filters, polarizing elements and the like.

Biometric device 33 includes the following sequence of elements: antifouling layer 16, hydrochromic layer 15 and image sensor 10.

Biometric device 34 includes the following sequence of elements: hydrochromic layer 15, image sensor 10 and authentication module 23.

Biometric device 35 includes the following sequence of elements: hydrochromic layer 15, optics 21 and image sensor 10.

Biometric device 36 includes the following sequence of elements: antifouling layer 16, hydrochromic layer 15, light transparent phosphorescent layer 17, optics 21, image sensor 10 and wireless transmitting layer 20.

Biometric device 37 includes the following sequence of elements: antifouling layer 16, hydrochromic layer 15, optics 21, image sensor 10 and image processor 22.

Biometric device 38 includes the following sequence of elements: hydrochromic layer 15, optics 21, light transparent phosphorescent layer 17, optics 21, image sensor 10 and image processor 22.

Biometric devices 50, 51, 52, 53, 54, 55, 56, 57 and 58 of FIG. 4 differ from biometric devices 30-38 of FIG. 1 by (a) having a gap between image sensor 10 and/or optics 21 and one or more other parts of the biometric device, and by (b) having a moisture sensor 15' instead of hydrochromatic layer 15. The moisture sensor that includes a hydrochromatic compound.

FIG. 5 biometric devices 60 and 61 as well as a cross section of a device 62 (such as but not limited to a smartphone) that includes moisture sensor 15' and image sensor 10. The device 62 may include any combination of any of biometric devices 30-38, 59-60.

Biometric device 60 includes moisture sensor 15', image sensor 10, wireless transmitting layer 20, image processor 22 and authentication module 23.

Biometric device 61 includes moisture sensor 15', image sensor 10, wireless transmitting layer 20, image processor 22 and authentication module 23.

Figure 2:
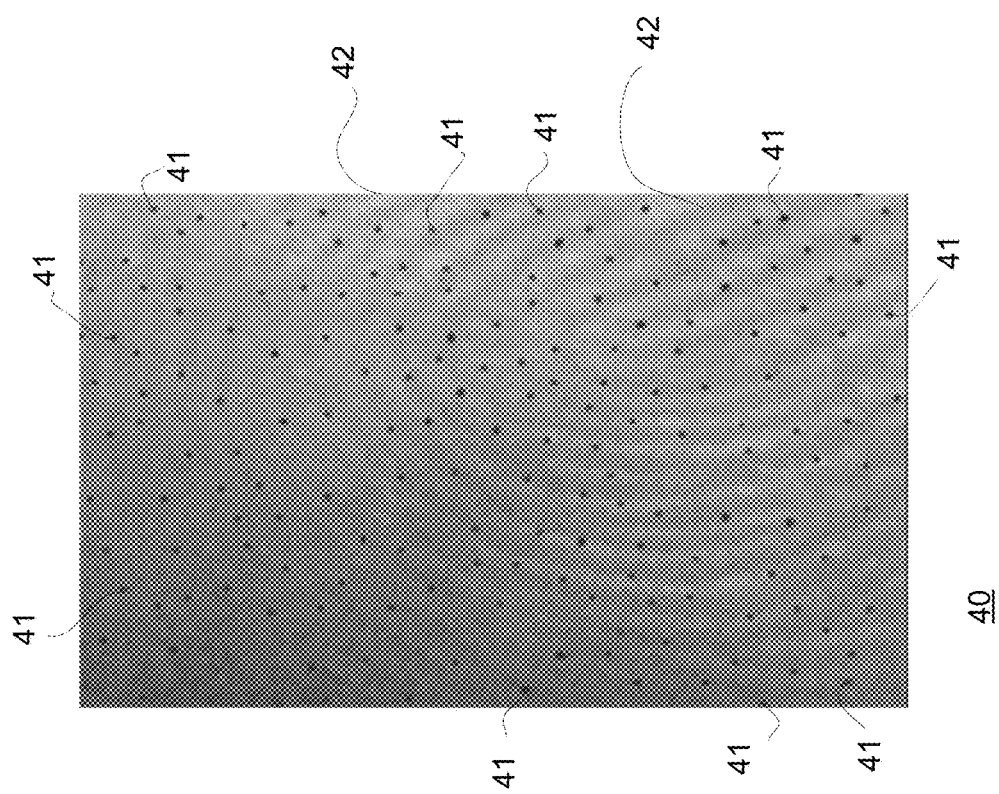
FIG. 2 is an image of a finger brought in contact with a rectangular piece hydrochromic sheet and acquired using a camera according to an embodiment of the invention.

FIG. 2 is an image of a finger brought in contact with a rectangular piece hydrochromic sheet and acquired using a camera according to an embodiment of the invention. The image includes topographic information 42 as well as information about the location of the sweat glands—such as dots 41.

Figure 3:
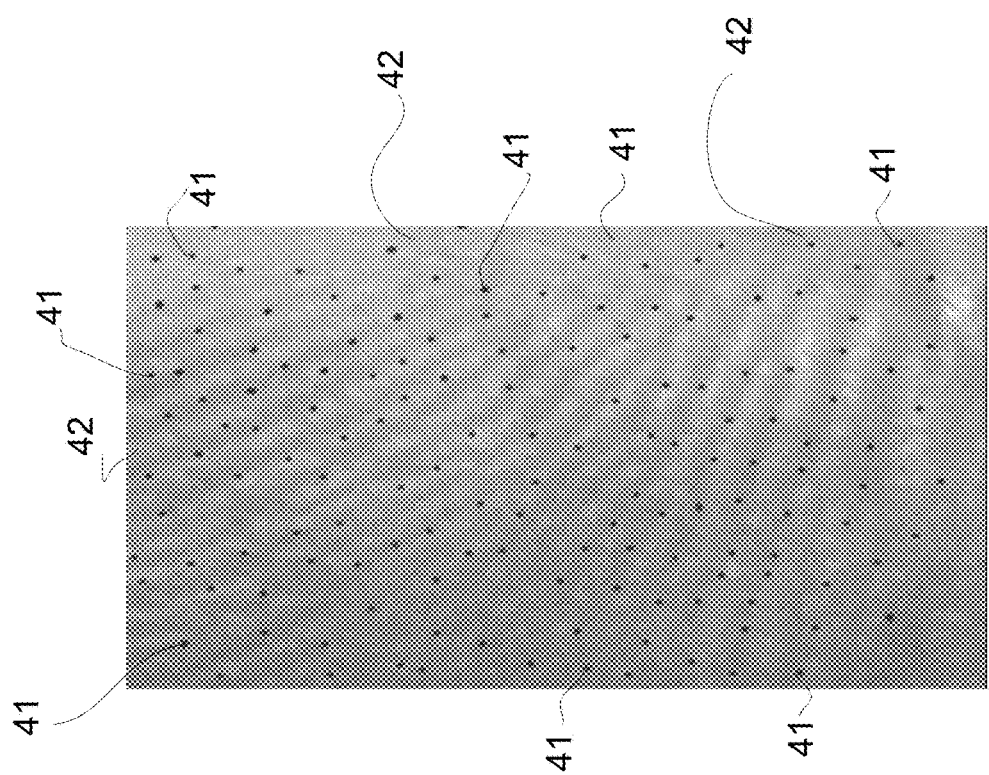
FIG. 3 is an image a skin segment of inner wrist brought in contact with a rectangular piece of hydrochromic sheet according to an embodiment of the invention.

FIG. 3 is an image a skin segment of inner wrist brought in contact with a rectangular piece of hydrochromic sheet according to an embodiment of the invention. The image includes topographic information 42 as well as information about the location of the sweat glands—such as dots 41.

FIG. 6 illustrates method 100 according to an embodiment of the invention.

Method 100 may start by step 110 of acquiring, by an image sensor and when a moisture sensor is contacted by an area of a skin of a person, an image that includes visual information about locations of sweat glands within the area of the skin of the person. The moisture sensor may include a hydrochromatic compound.

As indicated above—the image may be acquired when a sensor (even a sensor that differs from a moisture sensor) reacts to a chemical element associated with a sweat gland.

The area may be large enough to acquire enough information that can be used to authenticate a person. For example—if an area of skin of a given size (for example a square centimeter) is large enough to include enough sweat gland information to identify a person then the area of the skin should be of that size or may be bigger than that size. Alternatively—the person may scan more than a single area of skin to provide enough information for authentication.

The moisture sensor may include a hydrochromic layer or any other shaped arrangement of the hydrochromic compound.

The moisture sensor may be transparent in order to enable an image sensor to acquire the image while the area of the skin contacts the image sensor.

The image acquired during step 110 may also include additional visual information about the area of the skin.

The additional visual information may include includes topographic information related to the area of the skin. The topographic information refers to the three dimensional shape of the area of the skin. For example—if the area of the skin is a part of a finger than the topographic information may include a part of the fingerprint.

The additional visual information may include information about skin patterns.

Step 110 may be followed by step 120 of processing the image to provide a result.

The processing may include at least one of the following: (a) generating a sweat glands map, (b) authenticating a person based on the image, (c) authenticating a person based on the sweat glands map, (d) authenticating a person based on the locations of the sweat glands and based on additional visual information included in the image.

The authentication process may include comparing the information in the image to reference information such as a reference sweat glands map and/or reference fingerprint information (or other visual information such as topographic information) of a person.

Step 120 may be executed by the biometric device or by another device. The other device may receive the image by wireless transmission or any other manner.

Figure 7:
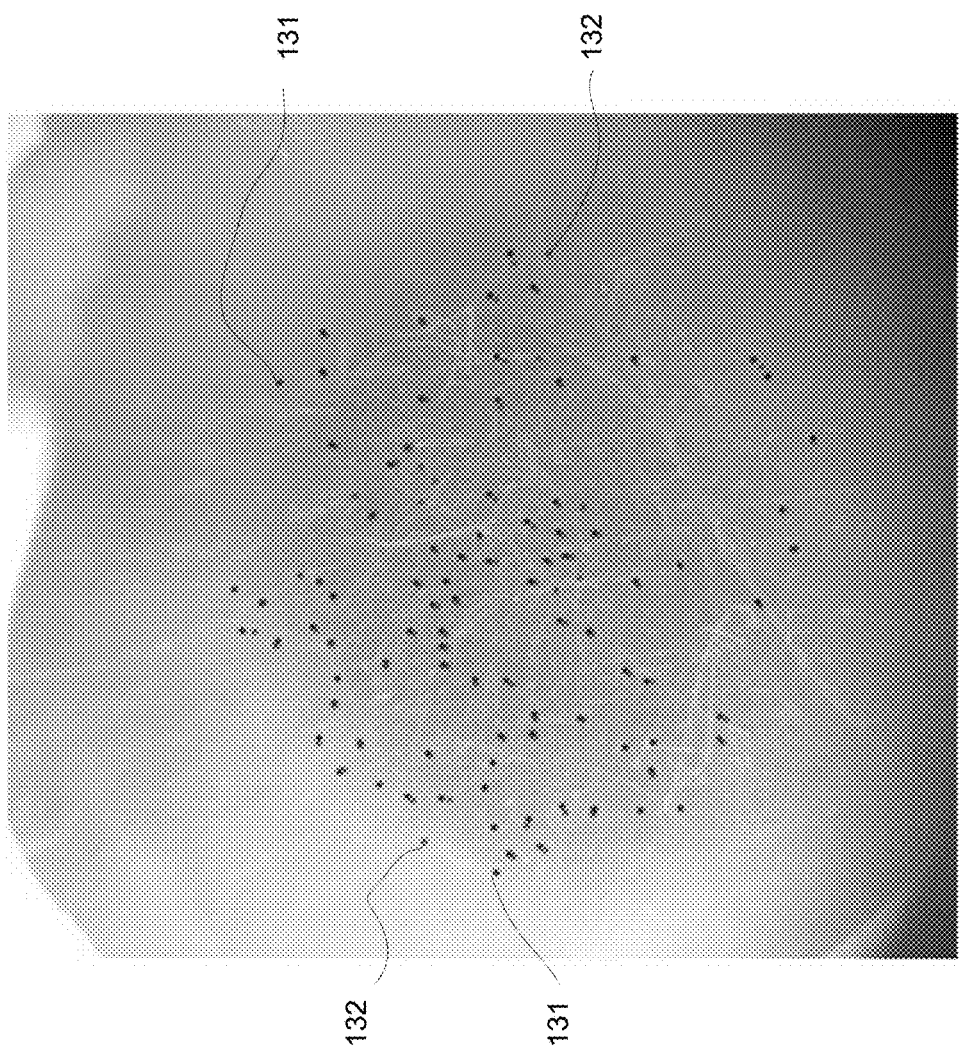
FIG. 7 presents a typical sweat gland images of two sample of the same finger that are overlaid one over the other according to an embodiment of the invention.

FIG. 7, presents a typical sweat gland images of two sample of the same finger that are overlaid one over the other. The two images (maps) are very similar to each other. Dots 131 provide an indication about the location of the sweat glands of the first sample. Dots 132 provide an indication about the location of the sweat glands of the second sample.

Figure 8:
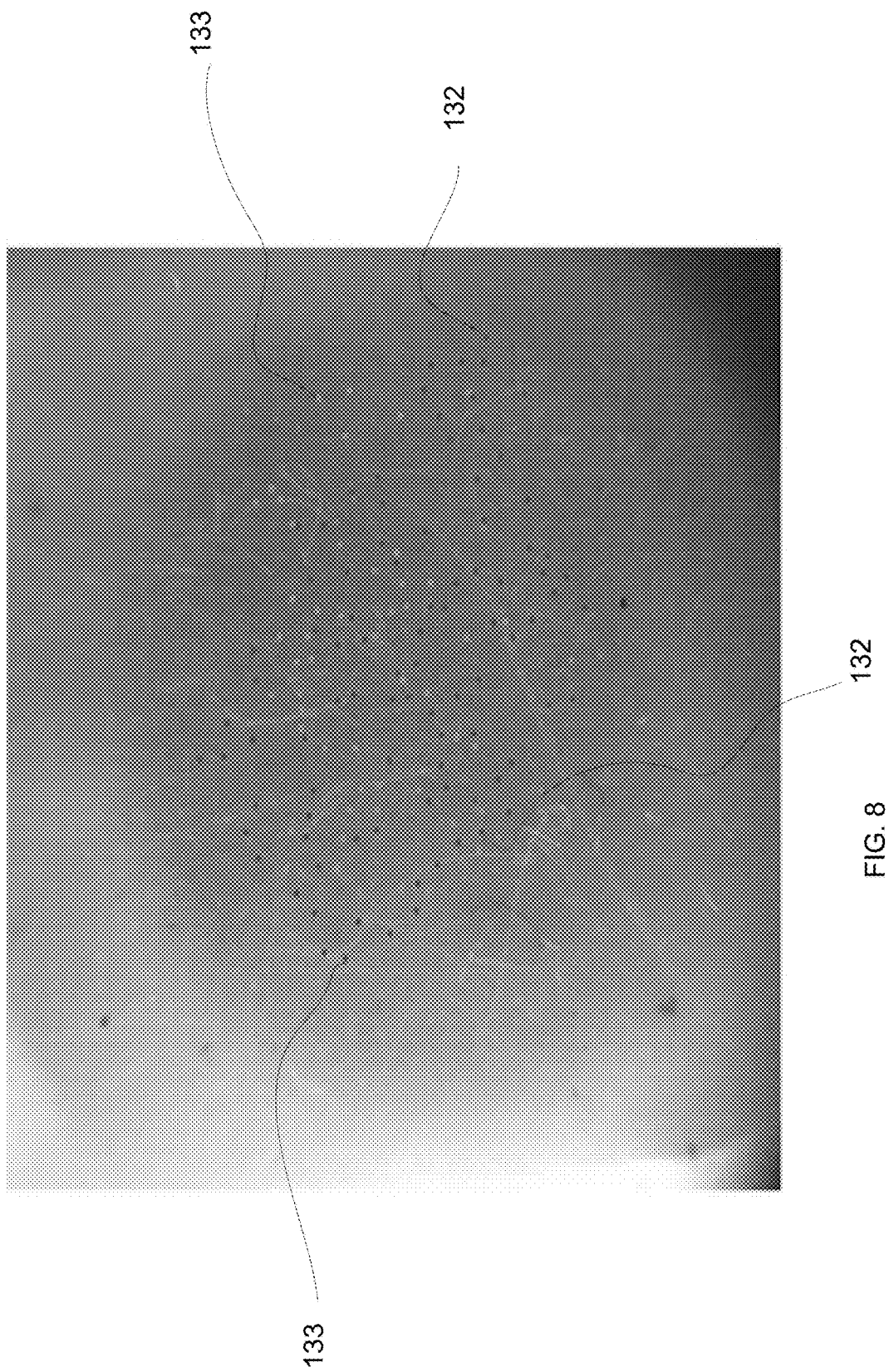
FIG. 8 presents a typical sweat gland images of two sample of two different fingers that are overlaid one over the other according to an embodiment of the invention.

FIG. 8 presents a typical sweat gland images of two sample of two different fingers that are overlaid one over the other. The two images (maps) are totally different.

Dots 131 provide an indication about the location of the sweat glands of the first sample. Dots 133 provide an indication about the location of the sweat glands of the second sample (of the other finger).

Figure 9:
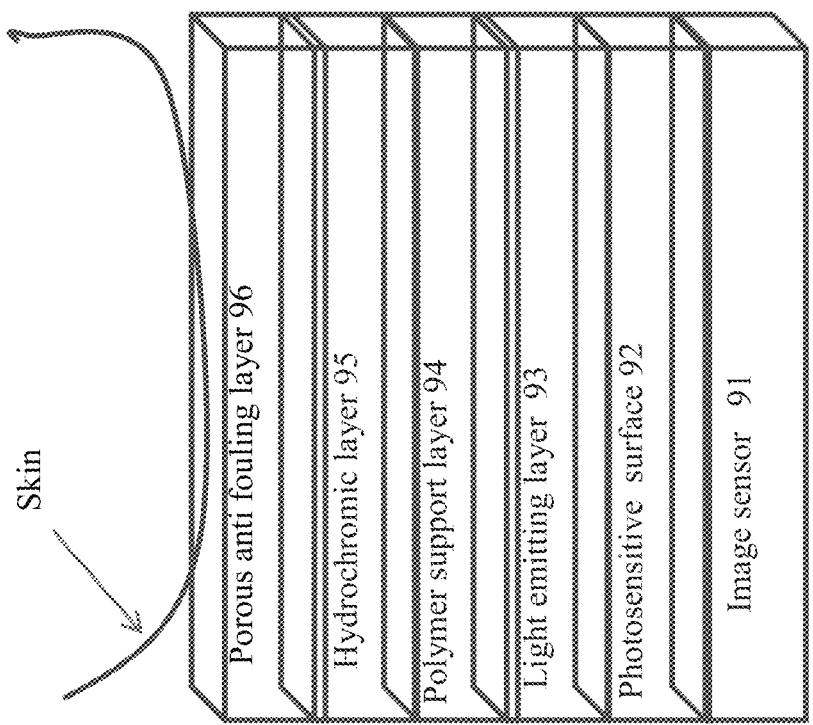
FIG. 9 illustrates a device according to an embodiment of the invention.

In FIG. 9 elements 91 and 92 represents the image sensor with its photosensitive surface. 93 is a transparent light source such as phosphor or tiny waveguide or fiber optic waveguide this layer can be located in different location. Layer 94 is a polymer that support the upper layers. 95 is Hydrochromic layer and or chemo chromic layer that are sensitive to the sweat, 96 is Porous anti fouling layer. It is noted that one or more of the elements of FIG. 9 may be merged to a single layer.

There may be provided a system that provides a seamless reliable identification that is based on sensor that detects the sweat gland map of the user.

The system may include a sweat gland based skin biometric imaging sensor, an image processor to process the sweat gland image, a memory for saving encrypted data and a communication module such as a short distance (between 1 centimeter and about 10 meters or more) electromagnetic or sound transmission element.

Sweat glands presents on most of the human skin, hence the device can be attached to the user body in various locations, such as behind the wearable watch that touches the skin, or on the band of the watch, it can also be embedded in a standalone bracelet, contained in a ring placed on a finger, it can also be embedded in clothing that is attached to the body like shirt that touch the shoulder. It can be attached to the user glasses where it touches the skin. See FIGS. 10A-1E, which presents some examples (watch 601, bracelet 602, ring 603, glasses 04 and shirt 605, where that system 200 can be placed.

Due to the fact that the sweat gland map is unique for each user combined with the fact that the sweat gland sensor can be attached to the user body in different locations and with the wireless or sonic capabilities of the apparatus, it can be used as wireless identifier (ID) for identifying a person. Namely it can be used as a reliable and seamless ID element that overcomes the need of using password or credit card type in order to access securely to mobile phone, or to conduct mobile payment, or to open confidential files, or to open secured entry doors, etc. or both.

It can also be combined with a fingerprint reader or another identification device, thus increasing substantially the ID performance.

The suggested system, for example, can be used to securely unlock a mobile phone once the mobile phone owner is close to the phone. It is done as follows; the owner wears a sensor with the suggested system, the suggested system may identify that the person that wears the system is the authorized person and communicates to the mobile phone that an authorized person is close to the mobile phone, hence the mobile phone will unlock him-self and will let the owner access to the mobile phone. In the case where the person is far from the mobile phone or he is not the authorized person, the mobile phone will stay locked.

Figure 11:
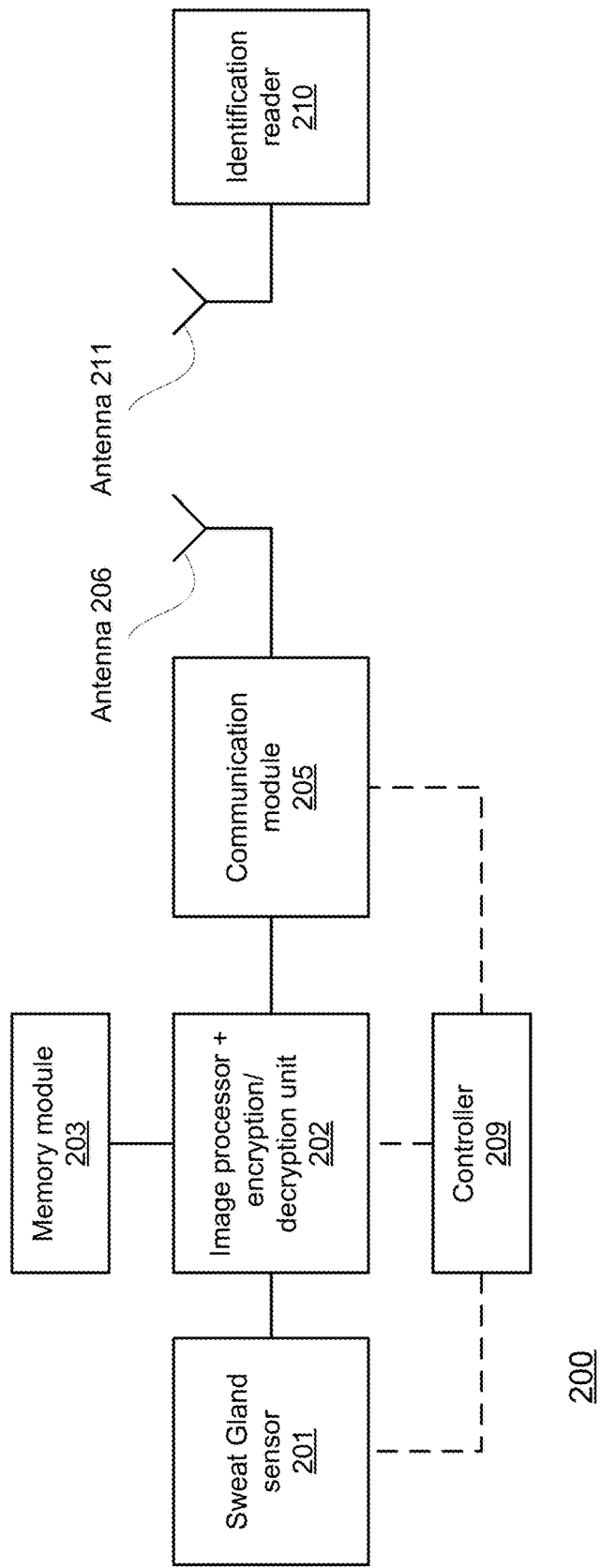
FIG. 11 illustrates an example of a system.

The system includes four main subsystems, see FIG. 11. For clarity we describe in details a typical case where the apparatus is embedded in a wearable digital watch such as presented in FIG. 10A.

However, it is relevant for all the other cases as well. There are two different mode of operation to use this system; registration mode and operation mode. Registration mode is when the user wears the watch for the first time and registers himself as the owner of the watch that has permission to access to predefined secure elements. The operation mode is when the user uses the watch day by day as an ID device.

In registration mode once the user wears the watch he notifies the device via control 204 that he wants to register as the owner of the device. If the device approves that he can start the registration process, sensor 201 captures the sweat gland map and other visual marks on the skin. This information is further analyzed in ISP 202 and it generates a sweat gland map as in FIGS. 2 and 3. Typical preprocess algorithm will be presented later. The image or the list of sweat gland and its coordinates is encrypted in 202 and is stored in memory unit 203. This process is being repeated several times until a satisfactory reference map and allowed variations are generated. This information will be used as reference in the operation mode.

In operation mode, when the user wears it, sensor 201 in FIG. 11 captures the sweat gland periodically and 202 analyze the image, to generate sweat gland map. The map is compared to the reference map stored in memory module 203.

The comparison can be made by different techniques, one being the correlation of the two images, its details will be presented later, and if there is a peak above a predefined threshold the user is defined as the owner of the device, this info is transmitted securely by 205.

To prevent spoofing or similar unauthorized actions it is preferred that the transmission will use short range transmission. Any other protection scheme for protecting the transmission may be applied. These techniques may refer to the manner of transmission (for example ultra-wide band transmission, frequency hopping and the like) and/or to the content of the transmission (data manipulations, encryption, and the like).

The ID reader 210 that receive the indication from 205 through antenna 206 and 211 that the authorized person is nearby and the ID reader 210 will provide him access to the desired material. The access can be access to unlock the mobile phone, access to open secure files in the phone or computer, permission to use mobile payment, access to open a secure door, etc. the type of service depends on ID reader 210. The communication between 205 and 210 can by near field communication (NFC) techniques or by activation of magnetic field or by any electromagnetic or Sonic wireless communication. If 210 is standard card reader the communication can be by using magnetic field.

It should be noted that in order to reduce power consumption of the watch, the system on the watch can operate only when there is a request from the reader, namely when the watch and the reader are close enough to each other, the watch receives a request from the reader to identify himself and then the watch starts to identify the watch holder by capturing his sweat gland map and compares it to the reference map. If there is a match, the watch transmits its user ID to the reader.

In order to save further power, the watch may sample the user skin once as long he did not take the watch off his hand. Once the user wears it on his hand, the watch indicates to the system on the watch to take sample from the user skin. This sample will be saved and will be erased once the user takes off the watch from his hand. A typical indication that the user takes the watch off is opening the locker of the watch which is normally located on the wrist of the watch.

Preprocess of the Image

As an example sensor 201 may include an image sensor such as a CCD or a CMOS sensor combined with a transparent polymer layer doped with a dispersion of reversible hydro-chromic, colorimetric moisture indicating composition optimized for fast response both in acquisition and in recovery time. The sensor when brought in contact with a skin area records the change in the moisture sensitive hydro-chromic layer which corresponds to local moisture distribution and enables the simultaneous acquisition of the sweat glands with the skin. In order to analyze the sweat gland map the skin image is considered as background noise and there is a need to filter it without affecting the sweat gland map image. There are various image processing techniques that can be used. We will present one process as an example.

Let denote the image that was captured as I(n,m) where n and m are the discrete coordinates, I is the intensity that is detected in location n,m. Let denote the image after the processing as IP(n,m)

I(n,m) undergoes the following process (thresholding):
a. If I(n,m)>TH_noise than IP(n,m)=1
b. Otherwise IP(n,m)=0

This process generates an image IP(n,m) were all the pixels that are related to sweat gland are equal to 1, and IP(n,m) ends up with clusters of pixels of value 1 where each cluster corresponds to sweat gland.

Correlation of Two Images

In the authentication process the captured processed image IP(n,m) is matched to the reference image IP_ref(n, m) the match process can be done by as an example calculating the cross correlation between the two images. Note the Imager should cover large enough area to allow identification despite small shifts of the sensor on the user body The correlation between the two images is done as follows:

$$R(k,l)=\text{sum}(IP(n-k,m-1)*IP\_ref(n,m))/(\text{Sqrt}(\text{sum}(IP(n,m))*IP(n,m))*\text{sum}(IP\_ref(n,m)*IP\_ref(n,m)))$$

Wherein n,m are summed over the range of 0 ... Nmax, 0 ... Mmax. Typical Nmax and M max can be 100 k,l are calculated in the range kmax, lmax. Wherein kmax and lmax depend how much the two images are expected to be shifted one compare to the other. In some cases, kmax and lmax can be 500.

If in the above range R(k,l) at least in one point kp,lp, R(kp,lp)>TH_match than we declare that the two images match, otherwise we declare no match and the person that wear this watch will not get permission to access.

Figure 12:
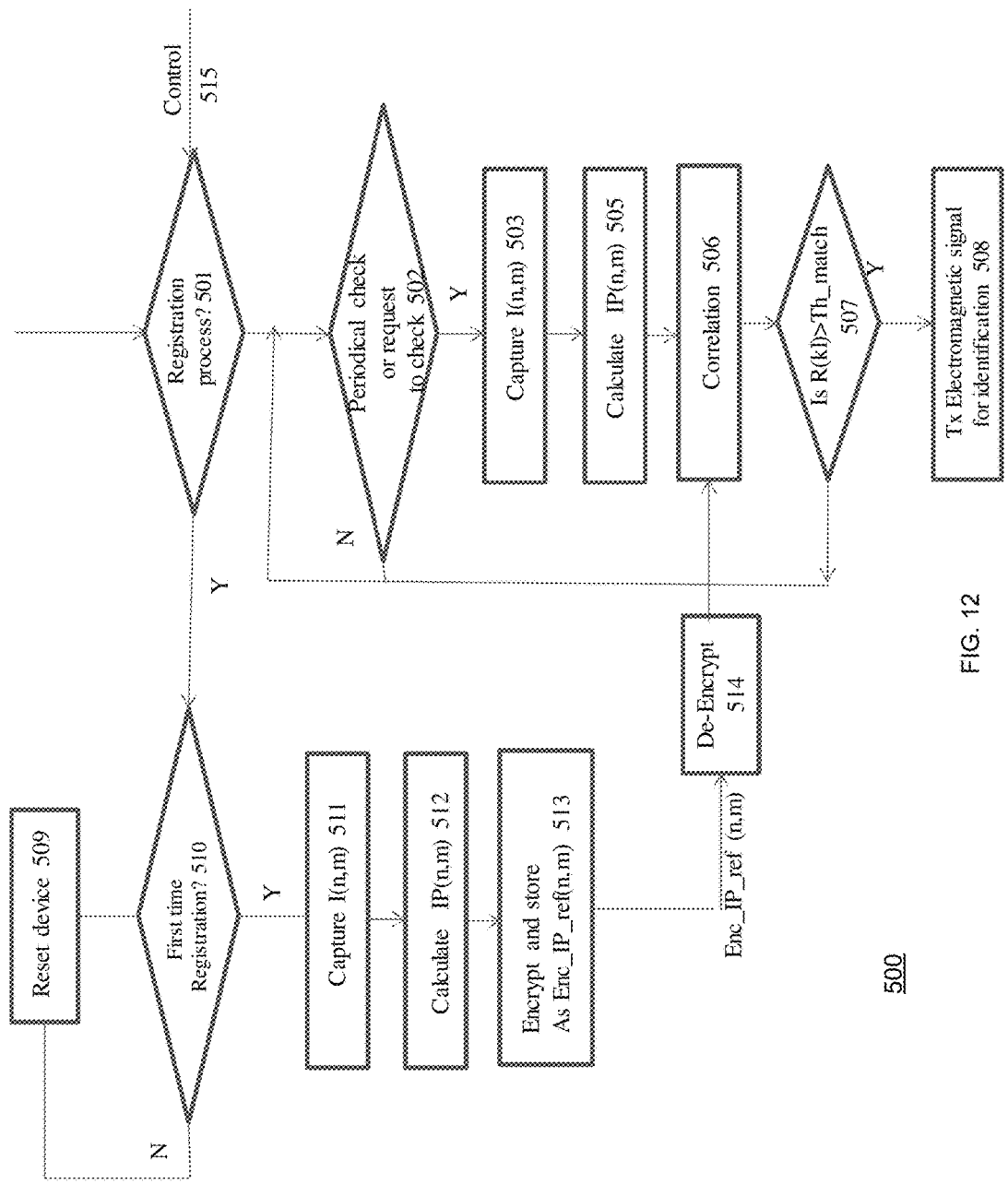
FIG. 12 illustrates an example of a method.

Referring to FIG. 12, which presents an example of a flowchart how the system operates.

In 501 the system checks if the device need to be registered (namely the system has factory parameters or someone reset the system) or already is registered.

If it is already registered in 502 the device checks the ID of the holder either periodically or upon request from the reader.

If the answer is yes (namely check user ID) in 503 the image of the sweat gland is captured and further processed in 505.

In 506 this image is compared to the ref IP_ref(n,m) by calculating in 506 the correlation function R(k,l) between the captured and the reference image, if in some point kp, lp there is a correlation greater than Th_match, the ID of the person holding the device is approved and in 508 this information is transmitted by near field electromagnetic signal to the reader by 205. The reader after analyzing the information received from the device will provide the permission to the user to access to secured staff.

It should be noted that in some cases process 505, 506 and 507 can be done in the reader. Any other partition between the process that is done in the device and in the reader can be used.

In case the process is registration, the sweat gland image of the user is captured in 511 and further processed in 512.

This image is encrypted in 513 and called Enc_IP_ref(n, m), this data is stored in secure memory 203. This sweat gland map image we consider it as the ID of the user.

Figure 13:
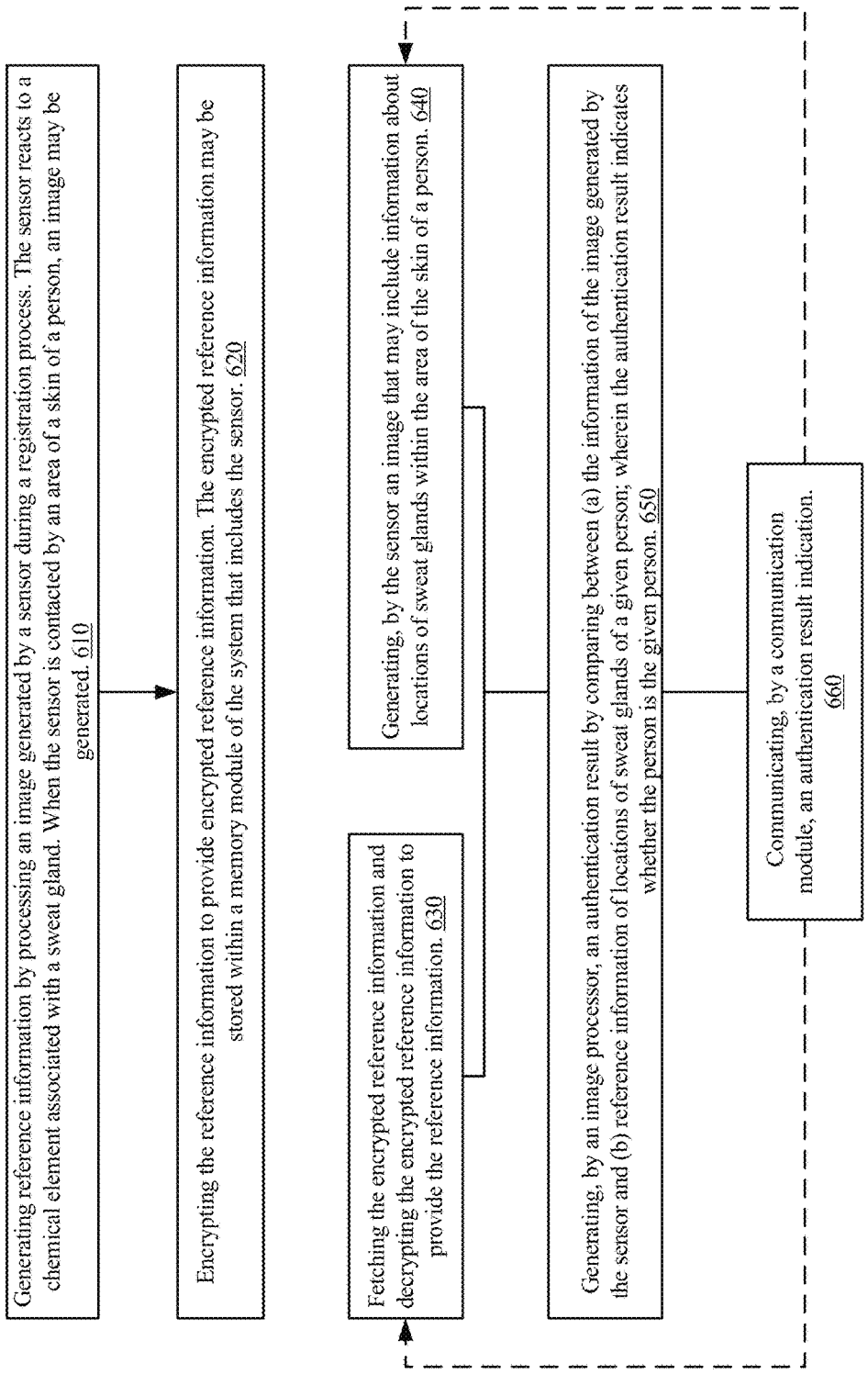
FIG. 13 illustrates an example of a method.

FIG. 13 illustrates method 600 according to an embodiment of the invention.

Method 600 may start by step 610 of generating reference information by processing an image generated by a sensor during a registration process. The sensor reacts to a chemical element associated with a sweat gland. When the sensor is contacted by an area of a skin of a person, an image may be generated. During the registration process the sensor generates the reference image. The reference image includes information about locations of sweat glands within the area of the skin of a given person—the person that performs the registration process.

Step 610 may include acquiring, by the sensor, an additional image of the area of the skin of the person. The additional image may include additional information about locations of sweat glands within the area of the skin of the person. Step 612 (in FIG. 6, block 612 is missing please add) may also include verifying the reference information by comparing between the reference information and the additional information Step 612 may be followed by step 620 of encrypting the reference information to provide encrypted reference information. The encrypted reference information may be stored within a memory module of the system that includes the sensor.

Step 610 may be followed by performing an authentication process.

The authentication process may start by steps 630 and 640.

Step 630 may include fetching the encrypted reference information and decrypting the encrypted reference information to provide the reference information.

Step 640 may include generating, by the sensor an image that may include information about locations of sweat glands within the area of the skin of a person.

Step 640 may be followed by step 650 of generating, by an image processor, an authentication result by comparing between (a) the information of the image generated by the sensor and (b) reference information of locations of sweat glands of a given person; wherein the authentication result indicates whether the person is the given person.

Step 650 may be followed by step 660 of communicating, by a communication module, an authentication result indication.

Step 610 may include generating a reference binary image. Step 650 may include thresholding the image generated by the sensor to provide a binary image and comparing the binary image to the reference binary image.

The reference information may include a reference image. Step 650 may include calculating a correlation between the reference image and the image acquired by the sensor.

Step 660 may include short range wireless communicating the authentication result indication.

Steps 630, 640, 650 and 660 may be repeated multiple times. The execution of these steps may be triggered by a controller—according to a predefined time schedule, in a random manner, in a pseudo random manner, in response to a request from the person, and the like.

Step 640 may also include obtaining additional visual information about the area of the skin. The additional visual information may include topographic information related to the area of the skin. The additional visual information may include information about skin patterns.

Step 650 may be also responsive to the additional visual information.

FIG. 14 describes a device that includes am embedded light guide (such as planar light guide 1410).

The sensing layer 1405 touches the skin 1401. The planar light guide 1410 is a transparent planner light guide which illuminates the sensing layer 1405.

The light source is an external light source such as led 1420

This illumination enables the image sensor 1415 to capture the map of sweat glands on 1405.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions.

It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements.

The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A biometric device, comprising:
   a sensor that reacts to a chemical element associated with a sweat gland; wherein when the sensor is contacted by an area of a skin of a person, the sensor is configured to acquire an image that comprises information about locations of sweat glands within the area of the skin of the person;
   an image processor that is configured to generate an authentication result by comparing between (a) the information of the image generated by the sensor and (b) reference information of locations of sweat glands of a given person; wherein the authentication result indicates whether the person is the given person;
   a communication module for communicating an authentication result indication; and
   a controller that is configured to trigger multiple authentication operations for acquiring multiple images of the area of the skin of the person and for generating multiple authentication results.

2. The biometric device according to claim 1 further comprising a memory module for storing encrypted reference information; and a decryption unit that is configured to decrypt the encrypted reference information to provide the reference information.

3. The biometric device according to claim 2 further an encryption unit that is configured to encrypt the reference information to provide the encrypted reference information.

4. The biometric device according to claim 3 wherein the image processor is further configured to generate the reference information by processing the image generated by the sensor during a registration process.

5. A biometric device, comprising: a sensor that reacts to a chemical element associated with a sweat gland; wherein when the sensor is contacted by an area of a skin of a person, the sensor is configured to acquire an image that comprises information about locations of sweat glands within the area of the skin of the person; an image processor that is configured to generate an authentication result by comparing between (a) the information of the image generated by the sensor and (b) reference information of locations of sweat glands of a given person; wherein the authentication result indicates whether the person is the given person;

a communication module for communicating an authentication result indication; wherein the sensor is configured to acquire an additional image of the area of the skin of the person; wherein the additional image comprises additional information about locations of sweat glands within the area of the skin of the person; and wherein the image processor is configured to verify the reference information by comparing between the reference information and the additional information.

6. The biometric device according to claim 1 wherein the reference information comprises a binary image; wherein the image processor is configured to threshold the image generated by the sensor to provide a binary image and to compare the binary image to the reference binary image.

7. The biometric device according to claim 1 wherein the reference information comprises a reference image; wherein the image processor is configured to calculate a correlation between the reference image and the image acquired by the sensor.

8. The biometric device according to claim 1 wherein the communication module is a short range wireless communication module.

9. The biometric device according to claim 1 wherein the sensor is a sensor that reacts with a chemical element included in sweat.

10. The biometric device according to claim 1 wherein the sensor is a moisture sensor that comprises a hydrochromic compound.

11. The biometric device according to claim 1, wherein the image further comprises additional visual information about the area of the skin.

12. The biometric device according to claim 11 wherein the additional visual information includes topographic information related to the area of the skin.

13. The biometric device according to claim 11 wherein the additional visual information includes information about skin patterns.

14. The biometric device according to claim 11 wherein the image processor is configured to generate the authentication result in response to the additional visual information.

15. The biometric device according to claim 1 wherein the sensor comprises a light guide.

16. The biometric device according to claim 1 wherein the sensor comprises a light guide that is transparent and positioned between a sensing layer of the sensor and an image sensor of the sensor.

17. The biometric device according to claim 1 comprising a memory module that is configured to store the image while the biometric device is worn by the person and to delete the image once the biometric device is removed from the person.

18. A method for biometric based authentication, the method comprises:

generating, by a sensor that reacts to a chemical element associated with a sweat gland and when the sensor is contacted by an area of a skin of a person, an image that comprises information about locations of sweat glands within the area of the skin of the person;

generating, by an image processor, an authentication result by comparing between (a) the information of the image generated by the sensor and (b) reference information of locations of sweat glands of a given person; wherein the authentication result indicates whether the person is the given person;

communicating, by a communication module, an authentication result indication; and triggering, by a controller, multiple authentication operations for acquiring multiple images of the area of the skin of the person and for generating multiple authentication results.

19. The method according to claim 18 comprising storing in a memory module encrypted reference information; and decrypting, by a decryption unit, the encrypted reference information to provide the reference information.

20. The method according to claim 19 comprising encrypting, by an encryption unit, the reference information to provide the encrypted reference information.

21. The method according to claim 20 comprising generating the reference information by processing the image generated by the sensor during a registration process.

22. The method according to claim 21 comprising acquiring, by the sensor, an additional image of the area of the skin of the person; wherein the additional image comprises additional information about locations of sweat glands within the area of the skin of the person; and verifying the reference information by comparing between the reference information and the additional information.

23. The method according to claim 18 wherein the reference information comprises a binary image; wherein the method comprises thresholding the image generated by the sensor to provide a binary image and comparing the binary image to the reference binary image.

24. The method according to claim 18 wherein the reference information comprises a reference image; wherein the method comprises calculating a correlation between the reference image and the image acquired by the sensor.

25. The method according to claim 18 wherein the communicating of the authentication result indication comprises short range wireless communicating the authentication result indication.

26. The method according to claim 18 wherein the generating of the image involves reacting with a chemical element included in sweat.

27. The method according to claim 18 wherein the generating of the image involves reacting to moisture; wherein the sensor comprises a hydrochromic compound.

28. The method according to claim 18, wherein the image further comprises additional visual information about the area of the skin.

29. The method according to claim 28, wherein the additional visual information includes topographic information related to the area of the skin.

30. The method according to claim 28, wherein the additional visual information includes information about skin patterns.

31. The method according to claim 28, wherein the generating of the authentication result is also responsive to the additional visual information.

32. The method according to claim 18 comprising preventing from acquiring additional images during a continuous period in which the sensor is worn by the person.

33. The method according to claim 18 comprising storing the image in a memory module and deleting the image once the sensor is removed from the person.

* * * * *